United States Patent
Kam et al.

(10) Patent No.: US 10,973,558 B2
(45) Date of Patent: Apr. 13, 2021

(54) SCREW INSERTION INSTRUMENT AND METHODS OF USE

(71) Applicant: K2M, Inc., Leesburg, VA (US)

(72) Inventors: Andrew Kam, Westmead (AU); Josh Rubin, Falls Church, VA (US); Olivia Angus, Pleasanton, CA (US); Mary Hayles, Brockport, NY (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 16/006,242

(22) Filed: Jun. 12, 2018

(65) Prior Publication Data

US 2018/0353224 A1 Dec. 13, 2018

Related U.S. Application Data

(60) Provisional application No. 62/518,094, filed on Jun. 12, 2017.

(51) Int. Cl.
| | |
|---|---|
| *A61B 17/70* | (2006.01) |
| *A61B 17/88* | (2006.01) |
| *A61B 17/56* | (2006.01) |
| *A61B 17/86* | (2006.01) |

(52) U.S. Cl.
CPC ...... *A61B 17/7082* (2013.01); *A61B 17/7085* (2013.01); *A61B 17/7091* (2013.01); *A61B 17/8897* (2013.01); *A61B 17/7032* (2013.01); *A61B 17/864* (2013.01); *A61B 2017/564* (2013.01)

(58) Field of Classification Search
CPC ............ A61B 17/7074; A61B 17/7076; A61B 17/7082
See application file for complete search history.

(56) References Cited

U.S. PATENT DOCUMENTS

| 4,838,282 A * | 6/1989 | Strasser ............... A61B 10/025 600/567 |
|---|---|---|
| 5,423,819 A | 6/1995 | Small et al. |
| 5,484,440 A | 1/1996 | Allard |

(Continued)

FOREIGN PATENT DOCUMENTS

| EP | 3501438 A1 | 6/2019 |
|---|---|---|
| WO | 2015186080 A2 | 12/2015 |
| WO | 2017127502 A1 | 7/2017 |

*Primary Examiner* — Nicholas J Plionis
(74) *Attorney, Agent, or Firm* — Lerner, David, Littenberg, Krumholz & Mentlik, LLP

(57) ABSTRACT

A screw insertion instrument includes a handle, a driving assembly, and a stylet. The driving assembly extends distally from the handle and includes a knob, a tubular body extending distally from the knob, and a driver including an elongated body extending through the knob and the tubular body. The elongated body has a proximal region operably coupled to the handle and a distal region extending distally beyond the tubular body and engageable with a pedicle screw. The stylet includes an elongated body positionable through first and second longitudinal bores defined through the handle and the driver, respectively. A proximal portion of the stylet is positionable adjacent the handle and a distal portion of the stylet extends distally beyond the driver and is positionable through a third longitudinal bore defined through the pedicle screw such that the distal portion of the stylet extends distally beyond the pedicle screw.

15 Claims, 12 Drawing Sheets

(56) References Cited

U.S. PATENT DOCUMENTS

| | | |
|---|---|---|
| 5,649,931 A | 7/1997 | Bryant et al. |
| 5,946,988 A | 9/1999 | Metz-Stavenhagen |
| 6,189,422 B1 | 2/2001 | Stihl |
| 6,312,394 B1 * | 11/2001 | Fleming, III ........ A61B 10/025 |
| | | 600/567 |
| 6,436,100 B1 | 8/2002 | Berger |
| 6,827,722 B1 * | 12/2004 | Schoenefeld ...... A61B 17/1622 |
| | | 606/104 |
| 7,296,500 B1 | 11/2007 | Martinelli |
| 7,572,264 B2 | 8/2009 | Null et al. |
| 7,758,584 B2 | 7/2010 | Bankoski et al. |
| 7,846,093 B2 | 12/2010 | Gorek et al. |
| 7,947,048 B2 | 5/2011 | Doll et al. |
| 8,002,798 B2 | 8/2011 | Chin et al. |
| 8,062,340 B2 | 11/2011 | Berrevoets et al. |
| 8,075,579 B2 | 12/2011 | Hamada |
| 8,100,916 B2 | 1/2012 | Kumar et al. |
| 8,221,431 B2 | 7/2012 | Chenaux |
| 8,231,635 B2 | 7/2012 | Sharifi-Mehr et al. |
| 8,262,662 B2 | 9/2012 | Beardsley et al. |
| 8,273,089 B2 | 9/2012 | Jackson |
| 8,308,729 B2 | 11/2012 | Nunley et al. |
| 8,343,165 B2 | 1/2013 | Berrevoets |
| 8,377,065 B2 | 2/2013 | Kuntz et al. |
| 8,394,108 B2 | 3/2013 | McLean et al. |
| 8,460,307 B2 | 6/2013 | Saidha et al. |
| 8,485,075 B1 | 7/2013 | Gauthier et al. |
| 8,512,344 B2 | 8/2013 | Hoffman et al. |
| 8,663,292 B2 | 3/2014 | Dec et al. |
| 8,714,056 B2 | 5/2014 | Landowski |
| 8,715,293 B2 | 5/2014 | Vandewalle |
| 8,747,411 B2 | 6/2014 | Mitchell |
| 8,814,914 B2 | 8/2014 | Miller et al. |
| 8,852,239 B2 | 10/2014 | Jackson et al. |
| 8,858,605 B1 | 10/2014 | Glatzer et al. |
| 8,894,655 B2 | 11/2014 | Fallin et al. |
| 9,131,946 B2 | 9/2015 | Larche et al. |
| 9,242,357 B2 | 1/2016 | Nino et al. |
| 9,254,160 B2 | 2/2016 | Pakzaban et al. |
| 9,409,285 B2 | 8/2016 | Ivinson et al. |
| 9,433,445 B2 | 9/2016 | Ramsay et al. |
| 9,451,954 B2 | 9/2016 | Moore et al. |
| 9,526,553 B2 | 12/2016 | Bess et al. |
| 9,750,508 B1 * | 9/2017 | Barnes ............... A61B 17/1671 |
| 9,855,087 B2 | 1/2018 | Divincenzo et al. |
| 9,877,764 B2 | 1/2018 | Nino et al. |
| 10,194,967 B2 | 2/2019 | Baynham |
| 10,219,845 B2 | 3/2019 | Petit |
| RE47,348 E | 4/2019 | Chin et al. |
| 10,413,339 B2 | 9/2019 | Ramsay et al. |
| 10,433,883 B2 | 10/2019 | DiVincenzo et al. |
| 10,575,888 B2 | 3/2020 | Coillard-Lavirotte et al. |
| 10,667,849 B2 | 6/2020 | Koenig et al. |
| 10,687,881 B2 | 6/2020 | Paroth et al. |
| 2002/0091386 A1 * | 7/2002 | Martin ................. G06Q 10/107 |
| | | 606/278 |
| 2004/0138662 A1 | 7/2004 | Landry et al. |
| 2005/0137601 A1 * | 6/2005 | Assell ................ A61B 17/1671 |
| | | 606/79 |
| 2006/0122597 A1 * | 6/2006 | Jones ................. A61B 17/7002 |
| | | 606/86 A |
| 2007/0239159 A1 * | 10/2007 | Altarac ................ A61B 17/025 |
| | | 606/86 A |
| 2008/0045970 A1 | 2/2008 | Saidha et al. |
| 2008/0243133 A1 | 10/2008 | Heinz |
| 2009/0187194 A1 | 7/2009 | Hamada |
| 2009/0187220 A1 | 7/2009 | Hamada |
| 2009/0264895 A1 | 10/2009 | Gasperut et al. |
| 2009/0275954 A1 | 11/2009 | Phan et al. |
| 2010/0036381 A1 * | 2/2010 | Vanleeuwen ....... A61B 17/8805 |
| | | 606/80 |
| 2010/0204703 A1 | 8/2010 | Gao |
| 2010/0298838 A1 | 11/2010 | Walters |
| 2011/0054537 A1 * | 3/2011 | Miller ................ A61B 17/1655 |
| | | 606/279 |
| 2011/0257690 A1 | 10/2011 | Rezach |
| 2012/0055296 A1 | 3/2012 | Landowski |
| 2012/0198972 A1 | 8/2012 | Nino et al. |
| 2012/0203287 A1 | 8/2012 | Arambula et al. |
| 2012/0203288 A1 | 8/2012 | Lange et al. |
| 2012/0239052 A1 | 9/2012 | Beger et al. |
| 2013/0013003 A1 | 1/2013 | Carbone et al. |
| 2013/0276597 A1 | 10/2013 | Ivinson et al. |
| 2013/0276598 A1 | 10/2013 | Ivinson et al. |
| 2013/0310842 A1 | 11/2013 | Winkler et al. |
| 2013/0327190 A1 | 12/2013 | Laurenti et al. |
| 2014/0194886 A1 * | 7/2014 | Poulos ................ A61B 17/864 |
| | | 606/94 |
| 2014/0276891 A1 | 9/2014 | Defalco et al. |
| 2014/0276893 A1 | 9/2014 | Schaller et al. |
| 2014/0277164 A1 | 9/2014 | Ramsay et al. |
| 2014/0277188 A1 * | 9/2014 | Poulos ............... A61B 17/1655 |
| | | 606/304 |
| 2014/0277206 A1 | 9/2014 | Reitblat et al. |
| 2014/0277212 A1 * | 9/2014 | Dauster ............. A61B 17/7086 |
| | | 606/86 R |
| 2014/0324062 A1 | 10/2014 | Heuer et al. |
| 2014/0330315 A1 | 11/2014 | Butler et al. |
| 2015/0066084 A1 | 3/2015 | Petit |
| 2015/0094781 A1 | 4/2015 | Paroth |
| 2015/0164540 A1 * | 6/2015 | Higgins ......... A61B 17/320758 |
| | | 606/159 |
| 2015/0164569 A1 * | 6/2015 | Reitblat ............ A61B 17/7079 |
| | | 606/279 |
| 2015/0250521 A1 * | 9/2015 | Poker ................ A61B 17/7037 |
| | | 606/104 |
| 2015/0282855 A1 * | 10/2015 | Bess .................. A61B 17/8875 |
| | | 606/86 A |
| 2015/0367487 A1 | 12/2015 | Nino et al. |
| 2016/0101508 A1 | 4/2016 | Cutler |
| 2016/0296266 A1 * | 10/2016 | Chandanson ....... A61B 17/8875 |
| 2016/0354906 A1 | 12/2016 | Nino et al. |
| 2017/0105813 A1 | 4/2017 | Rash et al. |
| 2017/0128116 A1 | 5/2017 | Hansell et al. |
| 2017/0217000 A1 | 8/2017 | Dierickx et al. |
| 2017/0333093 A1 | 11/2017 | Krier et al. |
| 2018/0092671 A1 | 4/2018 | Krause et al. |
| 2018/0133871 A1 | 5/2018 | Farmer |
| 2018/0146982 A1 * | 5/2018 | Brockman ......... A61B 17/3421 |
| 2018/0146990 A1 | 5/2018 | Manzanares et al. |
| 2018/0177536 A1 * | 6/2018 | Divincenzo ........ A61B 17/7082 |
| 2018/0235677 A1 | 8/2018 | Kam et al. |
| 2018/0368892 A1 | 12/2018 | Marnay |
| 2018/0368893 A1 | 12/2018 | DiVincenzo et al. |
| 2019/0022833 A1 | 1/2019 | Macke et al. |
| 2019/0083147 A1 | 3/2019 | Hackathorn, II |
| 2019/0125421 A1 | 5/2019 | Smith et al. |
| 2019/0247102 A1 | 8/2019 | Biedermann |
| 2019/0298416 A1 | 10/2019 | Rezach |
| 2019/0336180 A1 | 11/2019 | Cahill |
| 2020/0268427 A1 | 8/2020 | Muser et al. |

* cited by examiner

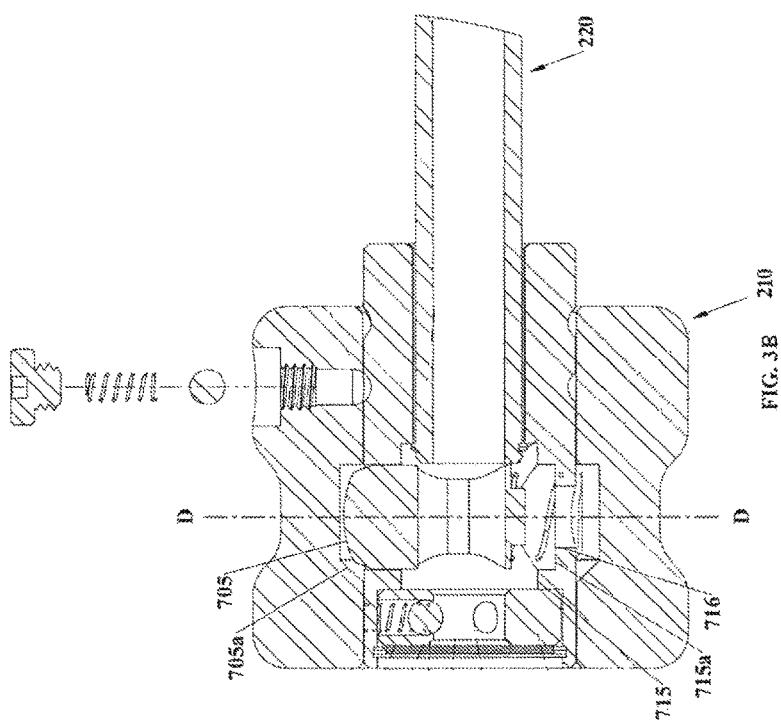

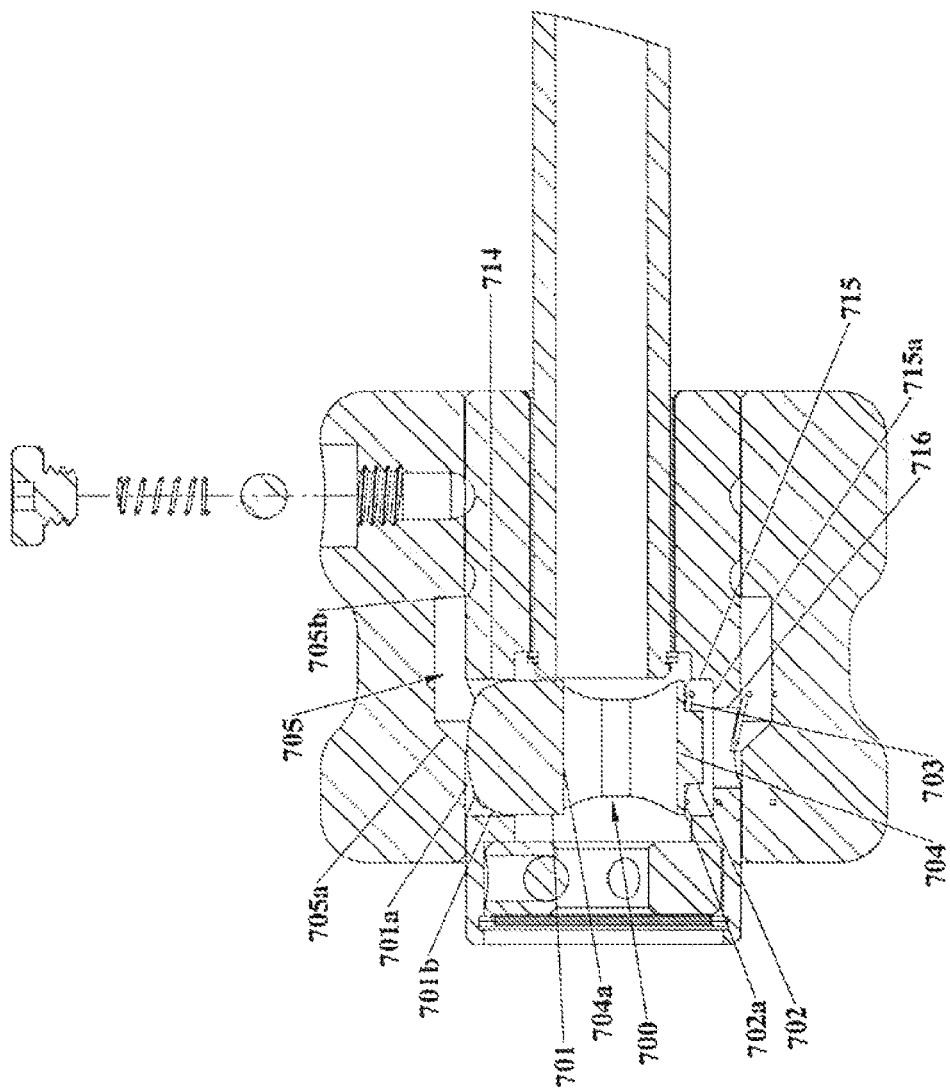

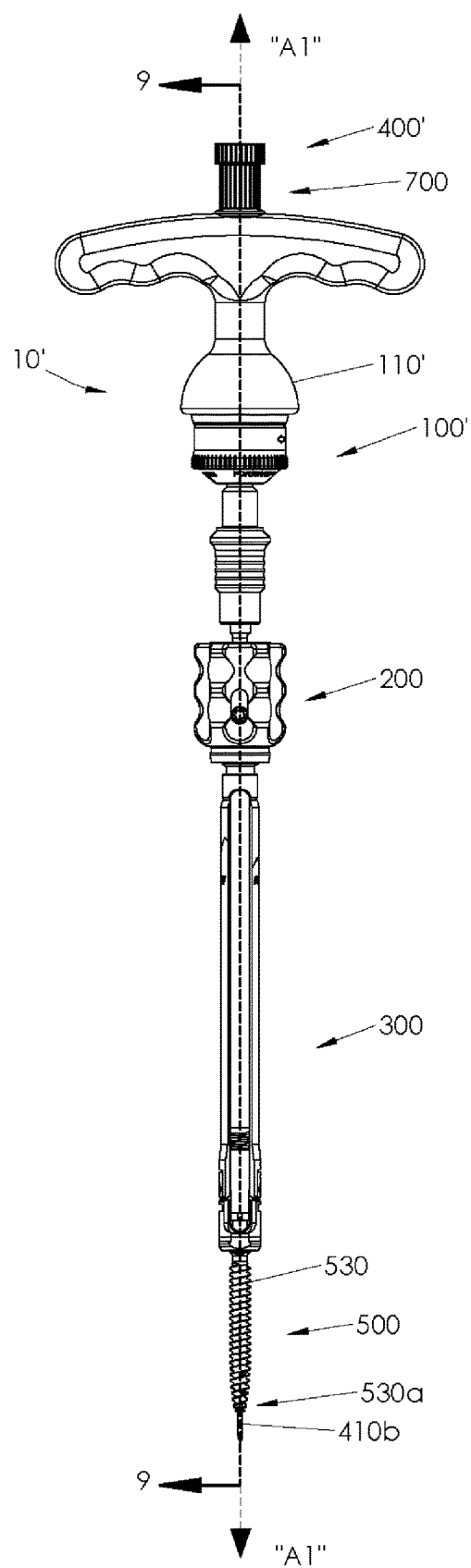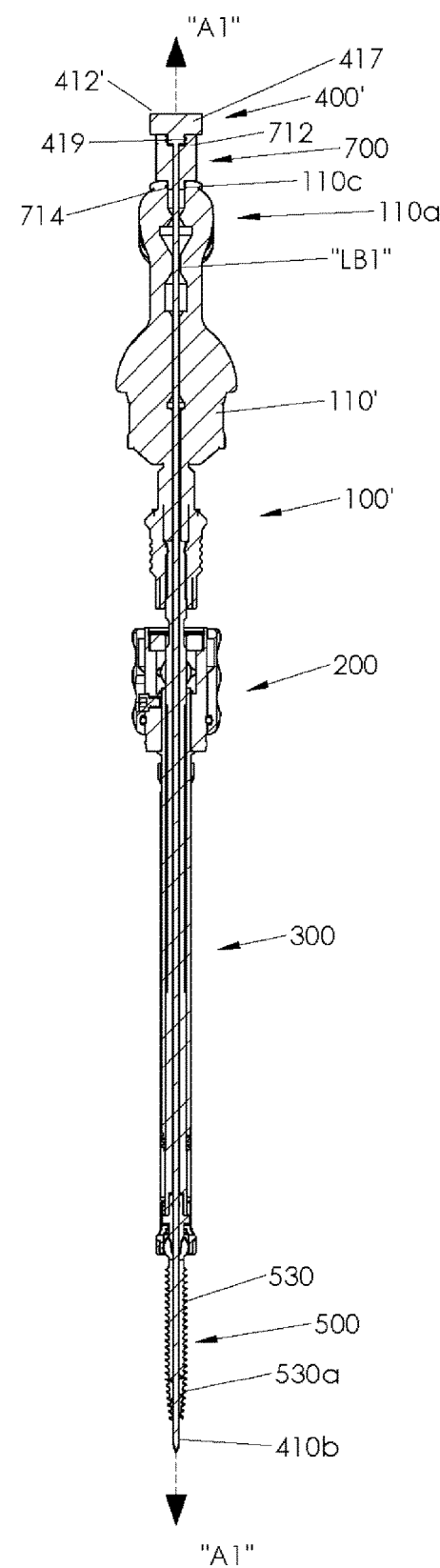
FIG. 8
FIG. 9

SCREW INSERTION INSTRUMENT AND METHODS OF USE

CROSS-REFERENCE TO RELATED APPLICATIONS

This application claims the benefit of, and priority to, U.S. Provisional Patent Application Ser. No. 62/518,094, filed Jun. 12, 2017, the entire contents of which are hereby incorporated herein by reference.

TECHNICAL FIELD

The present disclosure relates generally to surgical instruments and methods for orthopedic spine surgery and, more particularly, a screw insertion instrument and method for selectively coupling the screw insertion instrument to a pedicle screw, and introducing the pedicle screw into tissue.

BACKGROUND

Spinal fixation apparatus are widely employed in surgical processes for correcting spinal injuries and diseases. In order to facilitate stabilizing the spine and maintaining vertebral bodies in a desired alignment, implants, such as longitudinally linked rods, are secured to coupling elements which, in turn, are secured to vertebral bodies by fasteners, such as pedicle screws.

Many pedicle screws utilize a coupling element in the form of a tulip, which engages the pedicle screw head and is pivotable and rotatable in relation to the axis of the screw shank (e.g. polyaxial to the shank axis). While this ability more easily facilitates alignment of the tulip with the longitudinally linked rods, it may cause the pedicle screw to be difficult to handle. A means for ensuring the pedicle screw remains secured to an insertion instrument provides more positive control over the placement of the pedicle screw.

Prior to the placement of the pedicle screw into the vertebral body, many insertion instruments utilize devices, such as, for example, a guidewire to introduce the pedicle screw into the vertebral body and to control the trajectory of the pedicle screw so that it may be more accurately secured to the vertebral body.

Therefore, it would be desirable to facilitate introduction of the pedicle screw into the vertebral body efficiently, and in a minimally invasive manner, without the need for additional instruments.

SUMMARY

Accordingly, one aspect of the present disclosure is directed to a screw insertion instrument. The screw insertion instrument includes a handle, a driving assembly, and a stylet, and is configured for use with a pedicle screw. The handle defines a first longitudinal bore therethrough. The driving assembly extends distally from the handle and includes a knob, a tubular body extending distally from the knob, and a driver including an elongated body extending through the knob and the tubular body. The elongated body has a proximal region operably coupled to the handle and a distal region extending distally beyond the tubular body and engageable with a pedicle screw. The driver defines a second longitudinal bore therethrough. The stylet includes an elongated body positionable through the first and second longitudinal bores of the handle and the driver. A proximal portion of the stylet is positionable adjacent the handle and a distal portion of the stylet extends distally beyond the driver and is positionable through a third longitudinal bore defined through the pedicle screw such that the distal portion of the stylet extends distally beyond the pedicle screw.

The screw insertion instrument may further include an extension assembly including an elongated body extending distally from the knob of the driving assembly and adapted to receive the tubular body of the driving assembly therethrough. The elongated body of the extension assembly may have a distal portion configured to selectively engage the pedicle screw. In some embodiments, the elongated body of the extension assembly includes an internal threaded surface configured to threadably engage a threaded portion of the tubular body of the driving assembly.

The handle may include a gripping portion and a mounting sleeve. The mounting sleeve may have an internal housing configured to receive the proximal region of the driver of the driving assembly therein. The distal region of the driver may include a driving bit extending distally therefrom. The driving bit may be configured to engage a head of the pedicle screw. The knob of the driving assembly may be movable relative to the tubular body between a first position, in which the driver is movably supported within the knob and the tubular body, and a second position, in which the driver is fixedly supported within the knob and the tubular body.

The stylet may include a head at the proximal portion thereof and a tissue engaging member at the distal portion thereof. In embodiments, the head of the stylet includes a flange having a diameter greater than a diameter of the first longitudinal bore of the handle such that when the stylet is advanced distally therethrough, the flange abuts a proximal portion of the handle. In some embodiments, the screw insertion instrument further includes a clamping member configured to engage a proximal portion of the handle and the head of the stylet to selectively fix the stylet within the handle. In embodiments, the first longitudinal bore of the handle includes a threaded inner surface at a proximal end portion thereof, and the head of the stylet includes a threaded portion configured to threadably engage the threaded inner surface of the first longitudinal bore to selectively fix the stylet within the handle. In some embodiments, the screw insertion instrument further includes a spacer configured for passage of the elongated body of the stylet therethrough, and positionable between the head of the stylet and the handle.

According to another aspect, the present disclosure is directed to a screw insertion system comprising a pedicle screw and a screw insertion instrument. The pedicle screw includes a head and a threaded shank, and defines a longitudinal channel therethrough. The screw insertion instrument includes a handle, a driving assembly, and a stylet. The handle defines a first longitudinal bore therethrough. The driving assembly extends distally from the handle and includes a knob, a tubular body extending distally from the knob, and a driver including an elongated body extending through the knob and the tubular body. The elongated body has a proximal region operably coupled to the handle and a distal region extending distally beyond the tubular body and engageable with the head of the pedicle screw. The driver defines a second longitudinal bore therethrough. The stylet includes an elongated body positionable through the first and second longitudinal bores of the handle and the driver. A proximal portion of the stylet is positionable adjacent the handle and a distal portion of the stylet extends distally beyond the driver and is positionable through the longitudinal channel defined through the pedicle screw such that the distal portion of the stylet extends distally beyond the pedicle screw.

The pedicle screw may further include a tulip disposed around the head, and the screw insertion instrument may further includes an extension assembly. The extension assembly may include an elongated body extending distally from the knob of the driving assembly that may be adapted to receive the tubular body of the driving assembly therethrough. The elongated body of the extension assembly may have a distal portion configured to selectively engage the tulip of the pedicle screw.

The stylet may include a head at the proximal portion thereof. In some embodiments, the screw insertion instrument further includes a clamping member configured to engage a proximal portion of the handle and the head of the stylet to selectively fix the stylet within the handle. In some other embodiments, the screw insertion instrument further includes a spacer configured for passage of the elongated body of the stylet therethrough, and positionable between the head of the stylet and the handle.

According to yet another aspect, the present disclosure is directed to a method for inserting a screw into vertebral bone. The method includes advancing a driving assembly through an extension assembly that is coupled to a pedicle screw such that a knob of the driving assembly abuts a proximal portion of the extension assembly, a tubular body of the driving assembly is disposed within the extension assembly, and a driving bit of a driver of the driving assembly engages a head of the pedicle screw. The method also includes advancing a stylet through a handle that is coupled to the driver of the driving assembly such that an elongated body of the stylet is positioned through the handle, the driver, and the pedicle screw, a proximal portion of the stylet is positioned adjacent a proximal portion of the handle, and a distal portion of the stylet extends distally beyond a distal end of the pedicle screw. The method further includes penetrating vertebral bone with the distal portion of the stylet to create a pilot hole and introducing the pedicle screw into the vertebral bone through the pilot hole.

The method may further include rotating the knob of the driving assembly to secure the extension assembly to the driving assembly and/or actuating the knob of the driving assembly to rotatably fix the driver to the knob.

In some embodiments, the method further includes positioning a clamping member over the proximal portion of the handle to secure the proximal portion of the stylet to the handle. In some other embodiments, the method further includes threadably securing the proximal portion of the stylet into the proximal portion of the handle to secure the stylet to the handle. In certain embodiments, the method further includes positioning a spacer between the proximal portion of the stylet and the proximal portion of the handle such that a predetermined length of the distal portion of the stylet extends distally beyond the distal end of the pedicle screw.

BRIEF DESCRIPTION OF THE DRAWINGS

The above and other aspects, features, and advantages of the present disclosure will become more apparent in light of the following detailed description when taken in conjunction with the accompanying drawings in which:

FIG. 3B is an enlarged view of a knob assembly of the screw insertion instrument according to an exemplary arrangement.

FIG. 3C is an enlarged view of the knob assembly of FIG. 3B in a distal position.

FIG. 8 is a front view of the screw insertion instrument and the pedicle screw of FIG. 7, shown with a spacer, in accordance with yet another embodiment of the present disclosure;

FIG. 9 is a cross-sectional view of the screw insertion instrument and the pedicle screw of FIG. 8, taken along section line 9-9 of FIG. 8;

DETAILED DESCRIPTION OF THE EMBODIMENTS

Figure 1:
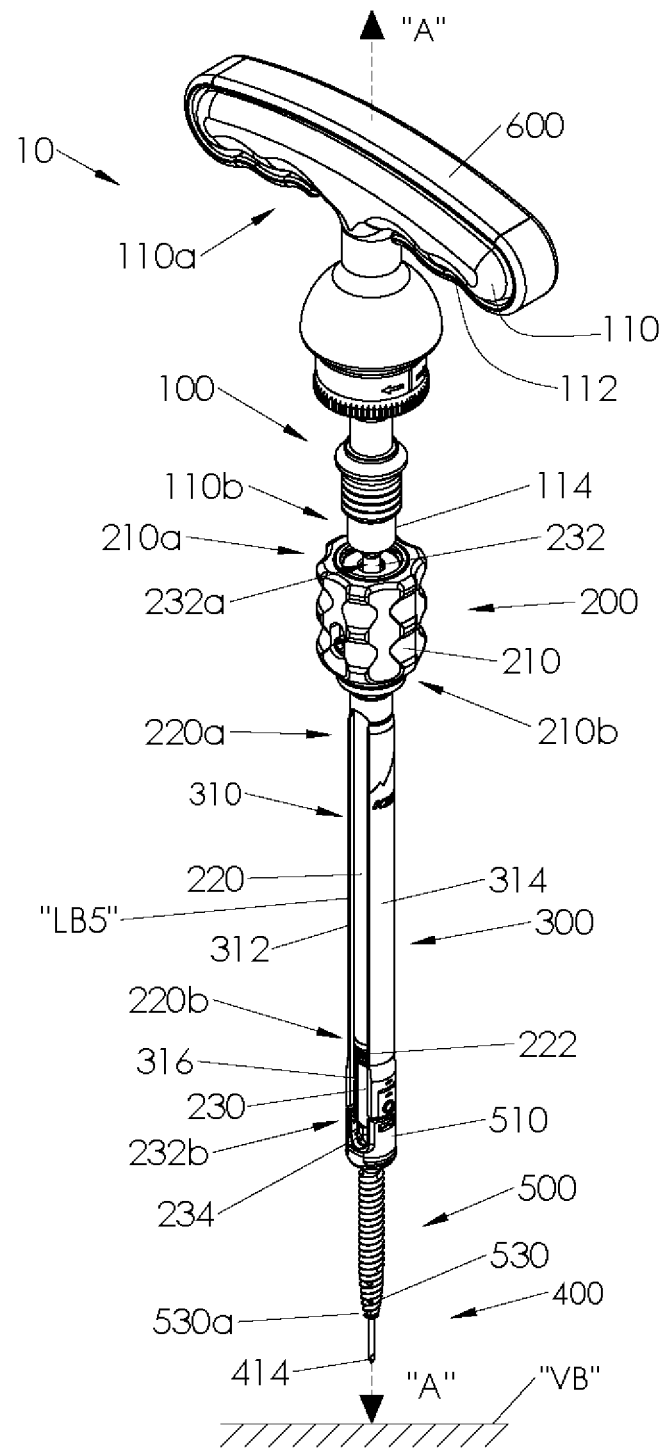
FIG. 1 is a perspective view of a screw insertion instrument coupled to a pedicle screw in accordance with an embodiment of the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to a portion of a device or component thereof that is closer to a clinician and the term "distal" will refer to a portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Referring now to the drawings, FIGS. 1-4 illustrate an embodiment of a screw insertion instrument 10 for selectively securing a pedicle screw 500 into tissue, such as, for example, bone and more specifically, vertebral bone "VB". The screw insertion instrument 10 generally includes a handle assembly 100, a driving assembly 200, an extension assembly 300, and a stylet 400 which are coaxially aligned along a longitudinal axis "A-A". A pedicle screw 500 is shown coupled to, and axially aligned with, the screw insertion instrument 10.

The handle assembly 100 includes a ratcheting handle 110 selectively attachable to the driving assembly 200 for mounting and/or securing one or more pedicle screws 500 into vertebral bone "VB," as will be further detailed below.

The ratcheting handle 110 of the handle assembly 100 includes a gripping portion 112 at a proximal portion 110a thereof and a mounting sleeve 114 at a distal portion 110b thereof. In one embodiment, the gripping portion 112 may be T-shaped, as illustrated in FIG. 1. In other embodiments, the gripping portion 112 may be any ergonomic shape which helps a clinician maintain a grip on the ratcheting handle 110. It is contemplated that the gripping portion 112 of the ratcheting handle 110 may include a symmetrical design to facilitate left and right hand use in operation.

Figure 4:
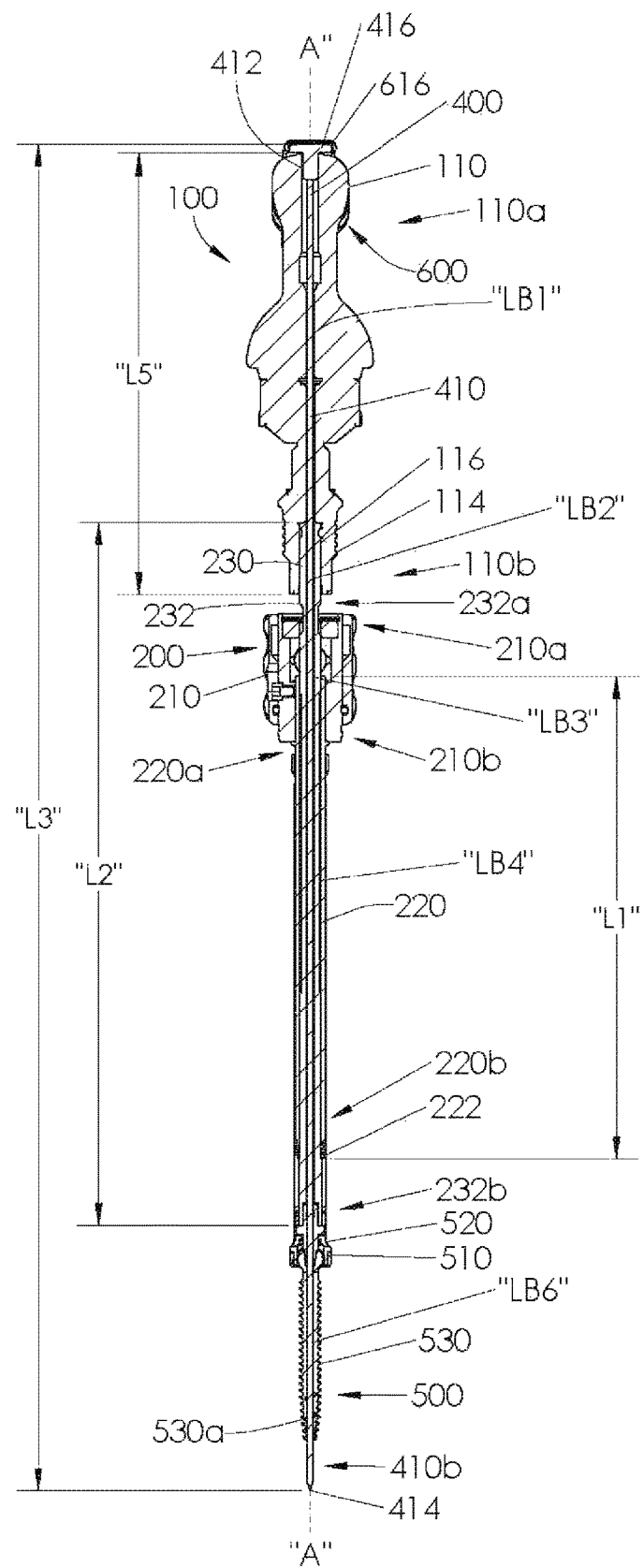
FIG. 4 is cross-sectional view of the screw insertion instrument and the pedicle screw of FIG. 3, taken along section line 4-4 of FIG. 3.

As specifically shown in FIG. 4, the ratcheting handle 110 of the handle assembly 100 defines a first longitudinal bore "LB1" extending between the proximal portion 110a and the distal portion 110b thereof. The first longitudinal bore "LB1" of the ratcheting handle 110 is axially aligned along the longitudinal axis "A-A" (i.e., coaxial with axis "A-A") and includes a diameter configured to rotatably and translatably support the stylet 400, as will be further detailed below. The mounting sleeve 114 of the ratcheting handle 110 includes an internal housing 116 configured to receive a driver 230 of the driving assembly 200 to operably couple the ratcheting handle 110 with the driving assembly 200. The internal housing 116 of the mounting sleeve 114 may be coupled to the driver 230 of the driving assembly 200 using any suitable techniques including, but not limited to, friction fitting and snap fitting.

With continued reference to FIGS. 1-4, the driving assembly 200 includes a knob 210, a tubular body 220, and a driver 230 longitudinally extending through the knob 210 and the tubular body 220. The knob 210 includes a proximal section 210a and a distal section 210b, and the tubular body 220 includes a proximal segment 220a and a distal segment 220b. The proximal segment 220a of the tubular body 220 is supported on the distal section 210b of the knob 210 and extends distally therefrom. In embodiments, the knob 210 is slidably coupled with the proximal segment 220a of the tubular body 220.

The driver 230 of the driving assembly 200 includes an elongated body 232 having a proximal region 232a and a distal region 232b. The proximal region 232a of the driver 230 is shaped and dimensioned for selective mounting within the internal housing 116 of the mounting sleeve 114 of the ratcheting handle 110, as discussed above. The distal region 232b of the driver 230 includes a driving bit 234 extending distally therefrom. The driving bit 234 of the driver 230 is configured to engage a head 510 of the pedicle screw 500 such that a threaded shank 530 of the pedicle screw 500 is in mechanical cooperation with the driver 230. The driving bit 234 of the driver 230 may have any configuration known in the art to transmit rotational motion of the driver 230 to the head 510 of the pedicle screw 500. Such configurations may be features, such as shaped cavities or protrusions that are square, hex, pozidrive, or the like, that are engageable with a corresponding feature of the head 510 of the pedicle screw 500 to enable the driver 230 to control rotation of the pedicle screw 500 and/or aid in the insertion or removal of the pedicle screw 500 into or out of the vertebral bone "VB." For a more detailed description of suitable driving assemblies, reference can be made, for example, to U.S. Pat. No. 8,308,729, filed Jun. 11, 2009, the entire contents of which are hereby incorporated by reference herein.

As specifically shown in FIG. 4, the elongated body 232 of the driver 230 defines a second longitudinal bore "LB2" extending between the proximal region 232a and the distal region 232b thereof. The second longitudinal bore "LB2" of the elongated body 232 of the driver 230 and the first longitudinal bore "LB1" of the ratcheting handle 110 of the handle assembly 100 are coaxially aligned along the longitudinal axis "A-A" and each includes a diameter configured to rotatably and translatably support the stylet 400, as will be further detailed below.

The knob 210 of the driving assembly 200 defines a third longitudinal bore "LB3" extending between the proximal section 210a and the distal section 210b thereof, and the tubular body 220 of the driving assembly 200 defines a fourth longitudinal bore "LB4" extending between the proximal segment 220a and the distal segment 220b thereof. The third longitudinal bore "LB3" of the knob 210 and the fourth longitudinal bore "LB4" of the tubular body 220 are coaxially aligned along the longitudinal axis "A-A" and each includes a diameter configured to selectively rotatably and translatably support the driver 230 of the driving assembly 200; in other words, "LB1-LB4" are coaxially aligned. Specifically, the knob 210 is repositionable between a proximal position and a distal position relative to the tubular body 220. When the driver 230 is translated through the knob 210 and the tubular body 220, and the knob 210 is in the proximal position relative to the tubular body 220, the knob 210 is rotatable with respect to the driver 230 about the longitudinal axis "A-A." When the driver 230 is translated through the knob 210 and the tubular body 220, and the knob 210 is advanced to the distal position relative to the tubular body 220, the knob 210 is mechanically engaged with the driver 230 such that the knob 210 and the tubular body 220 are rotatably and translatably fixed with respect to the driver 230 about the longitudinal axis "A-A." For a more detailed description of the knob 210, reference can be made, for example, to U.S. Pat. No. 9,526,553, filed Apr. 4, 2014, the entire contents of which are incorporated by reference herein.

Figure 3:
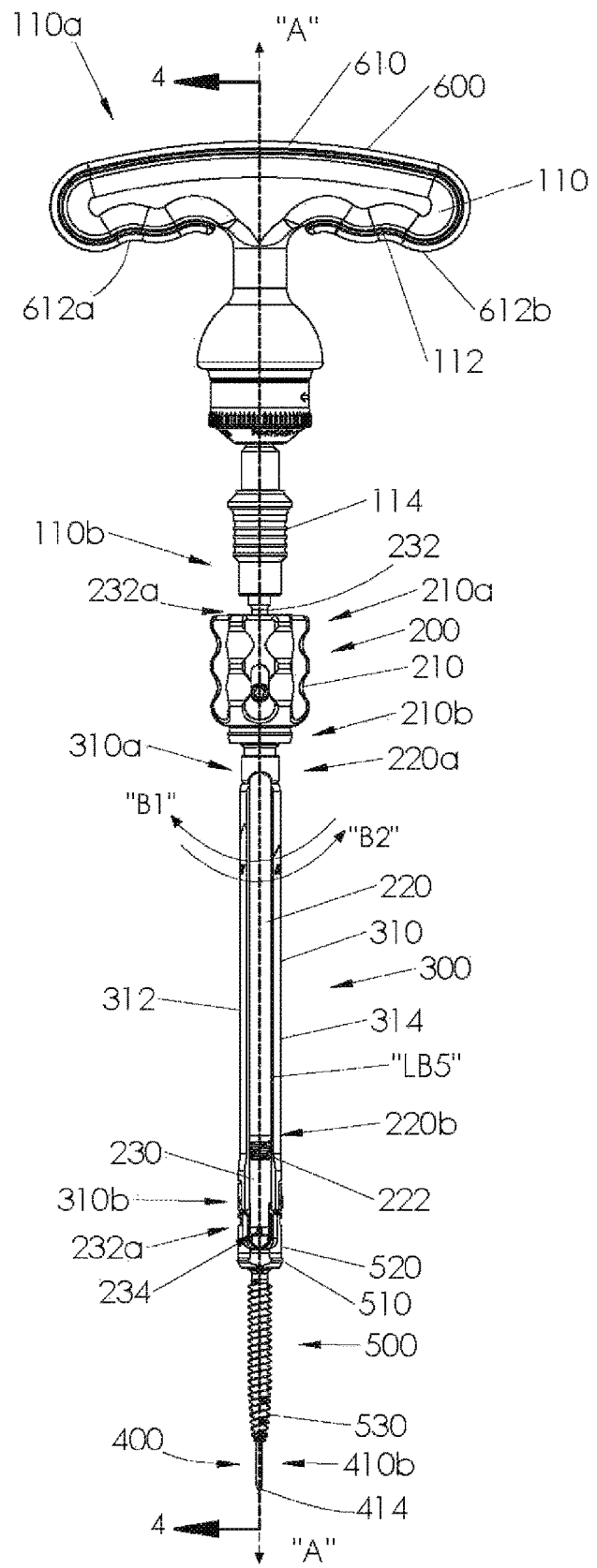
FIG. 3 is a front view of the screw insertion instrument and the pedicle screw of FIG. 1.
Figure 3A:
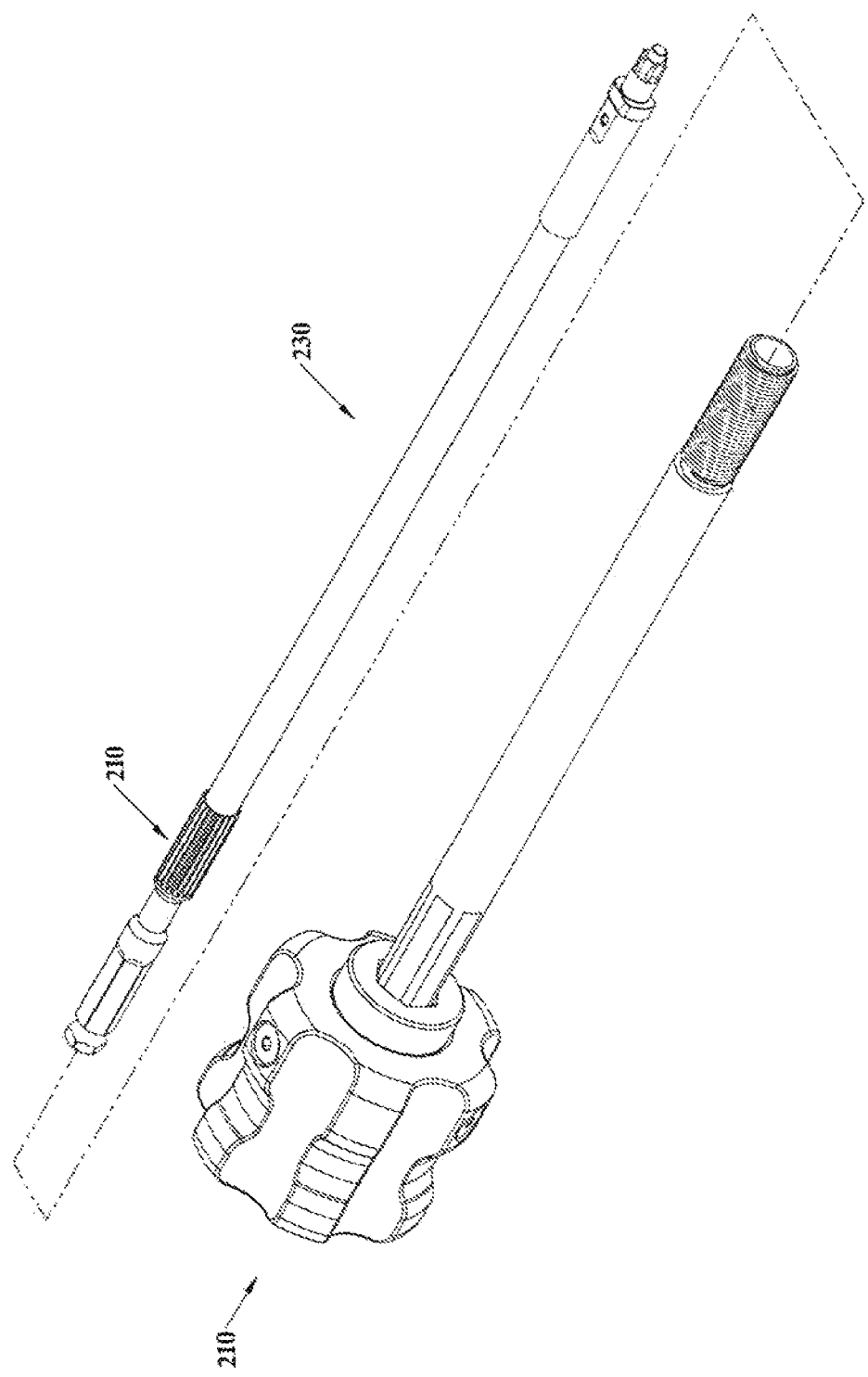
FIG. 3A is an exploded view, with parts separated, of a portion of the screw insertion instrument.

As shown in FIG. 3A, driver 230 is disposed within tubular body 220 and knob 210. Longitudinal splines 231 are arranged radially around a portion of driver 230.

FIGS. 3B and 3C illustrate an engagement button assembly included in the knob 210. The engagement button assembly includes an engagement button 701 and an engagement button spring 703. Engagement button 701 is cylindrical in cross section and includes proximal and distal ends. The outer diameter of engagement button 701 is such that it engages first through hole 714 by a slip fit. The proximal end of engagement button 701 includes a spherical dome 701 a. One non-limiting embodiment of spherical dome 701 a is of generally large radius; however, spherical dome 701 a can be of any radius greater than or equal to the outer diameter of button 700. The proximal end of engagement button 700 further includes a chamfer 701 b. Chamber 701 b runs circumferentially about the proximal end of engagement button 700 such that the transition from the outer diameter of engagement button 700 to spherical dome 701 a is more gradual. Chamfer 701 b may include any angle with respect to the outer surface of engagement button 700 between zero (0) and ninety (90) degrees such that chamfer 701 b extends radially inward from the outer surface of engagement button 700. The distal end of engagement button 700 further includes boss 702. Boss 702, having proximal and distal ends, extends distally from the distal end of engagement button 700 and includes an outer diameter less than that of the outer diameter of engagement button 700, and such that the distal end of boss 702 may pass through second hole 716. The proximal end of boss 702 extends from a face 702 a, which includes the annular space between the outer diameter of engagement button 700 and the outer diameter of boss 702. Engagement button 700 further includes a bore 704 having open proximal and distal ends. Bore 704 extends normal to the outer surface of engagement button 700 and includes a smooth inner bore for approximately ¾ of its circumference on the surface closest to the distal end of engagement button 700. The remaining approximately ¼ circumference of the inner bore closes to the proximal end of engagement button 700 includes splines 704 a configured such that they may engage splines 231 of driver 230 when driver 230 is disposed therein. Splines 231 extend from the open proximal end to the open distal end of engagement button 700 along axis.

Engagement button spring 703, having proximal and distal ends, is disposed between face 702 a of engagement button 700 and surface 715 a of counterbore 715 when engagement button 700 is disposed within first through hole 214. The proximal end of engagement button spring 703 abuts face 702 a and the distal end of engagement button spring 703 abuts surface 715 a and biases engagement button 700 such that when knob 210 is in a proximal position engagement button 700 rests within groove 705 and is coaxially aligned with axis D-D (see FIG. 3B). In this position, splines 704 a are not engaged with splines 231 thus permitting knob 210 to rotate with respect to driver 230. Referring now to FIG. 3C, an illustration of knob 210 in a distal position is provided. As knob 210 is actuated to a distal position, chamfer 705 a of groove 705 acts against chamfer 701 b of engagement button 700 such that engagement button 700 is driven distally along axis D-D. In this distal position of knob 210, splines 704 a are engaged with splines 231 causing knob 210 to be in mechanical engagement (i.e. coupled and rotationally fixed) with driver 230 permitting the clinician to drive a pedicle screw into a vertebral body.

As illustrated in FIG. 4, the tubular body 220 of the driving assembly 200 includes a first length "L1" that is less than a second length "L2" of the elongated body 232 of the driver 230, such that when the driver 230 is advanced distally through the third longitudinal bore "LB3" of the knob 210 and the fourth longitudinal bore "LB4" of the tubular body 220, the distal region 232b of the elongated body 232 is extendable distally beyond the distal segment 220b of the tubular body 220.

With continued reference to FIGS. 1-4, the extension assembly 300 of the screw insertion instrument 10 includes an elongated body 310 having a proximal portion 310a and a distal portion 310b. The elongated body 310 is defined by a pair of extensions 312, 314 selectively coupled together by an end cap 315 at the proximal portion 310a of the elongated body 310. When the extensions 312, 314 are coupled together by the end cap 315, the elongated body 310 defines a fifth longitudinal bore "LB5" between the proximal portion 310a and the distal portion 310b thereof. The fifth longitudinal bore "LB5" of the elongated body 310 includes a diameter adapted to receive the tubular body 220 of the driving assembly 200 such that the proximal portion 310a of the elongated body 310 abuts the distal section 210b of the knob 210 of the driving assembly 200 when the tubular body 220 of the driving assembly 200 is advanced through the fifth longitudinal bore "LB5" of the elongated body 310. From this position, the driving assembly 200 and the extension assembly 300 may be selectively rotatably and translatably fixed about the longitudinal axis "A-A," as will be further detailed below.

In embodiments, the elongated body 310 includes an internal threaded surface 316 (FIG. 1) defined on each extension 312, 314. It is contemplated that the internal threaded surface 316 of each extension 312, 314 is configured to threadably engage a threaded portion 222 on the distal segment 220b of the tubular body 220 as the tubular body 220 of the driving assembly 200 is advanced through the fifth longitudinal bore "LB5" of the elongated body 310 of the extension assembly 300. In other embodiments, the internal threaded surface 316 of each extension 312, 314 may be configured to threadably engage a set screw (not shown) during a procedure, such as, for example, an internal rod reduction.

As illustrated in FIGS. 3 and 4, the pedicle screw 500 includes a head 510, a coupling element or tulip 520, and a threaded shank 530 extending distally from head 510. The tulip 520 of the pedicle screw 500 is configured to mechanically couple with the pair of extensions 312, 314 of the elongated body 310 of the extension assembly 300. For a detailed discussion of the construction of the pedicle screw 500, reference may be made, for example, to U.S. Patent Publication No. 2013/0013003, filed on Sep. 26, 2012, entitled "Polyaxial Bonescrew Assembly," the entire contents of which are incorporated herein by reference.

As specifically shown in FIG. 4, the pedicle screw 500 defines a sixth longitudinal bore "LB6" extending between the head 510 and the threaded shank 530 of the pedicle screw 500. The sixth longitudinal bore "LB6" of the pedicle screw 500 is coaxially aligned along the longitudinal axis "A-A" and includes a diameter configured to rotatably and translatably support the stylet 400, as will be further detailed below.

With reference again to FIGS. 1-4, in use, with the tulip 520 of the pedicle screw 500 coupled to the extension assembly 300, the driving assembly 200 may be rotatably and translatably fixed to the extension assembly 300 and the pedicle screw 500 such that rotational motion of the driver 230 of the driving assembly 200 may be transmitted to the pedicle screw 500. Specifically, the tubular body 220 of the driving assembly 200 is advanced through the fifth longitudinal bore "LB5" of the elongated body 310 of the extension assembly 300 until the driving bit 234 of the driver 230 of the driving assembly 200 is engaged with the head 510 of the pedicle screw 500. As the driver 230 engages the head 510, the proximal portion 310a of the elongated body 310 abuts the distal section 210b of the knob 210 of the driving assembly 200. From this position, the knob 210 is rotated in a clockwise direction "B1" (FIG. 3) relative to the longitudinal axis "A-A" to threadably engage the proximal portion 310a of the elongated body 310. The knob 210 is then moved to the proximal position relative to the tubular body 220 to securely fix the driving assembly 200, the extension assembly 300, and the pedicle screw 500.

With continued reference to FIGS. 1-4, the stylet 400 includes an elongated body 410 having a proximal portion 410a (FIG. 2) and a distal portion 410b (FIG. 3). In embodiments, the proximal portion 410a of the elongated body 410 includes a head 412 and the distal portion 410b of the elongated body 410 includes a tissue engaging member 414. The stylet 400 is selectively translatable through the first longitudinal bore "LB1" of the ratcheting handle 110 of the handle assembly 100 and the second longitudinal bore "LB2" of the elongated body 232 of the driver 230 of the driving assembly 200.

In embodiments, the stylet 400 includes a length "L3" that is greater than a combination of a length "L5" of the ratcheting handle 110 and the length "L2" of the elongated body 232 of the driver 230 such that when the stylet 400 is advanced distally through the first longitudinal bore "LB1" of the ratcheting handle assembly 100 and the second longitudinal bore "LB2" of the elongated body 232 of the driver 230, the distal portion 410b of the elongated body 410 of the stylet 400 is extendable distally beyond the distal region 232b of the elongated body 232 of the driver 230. Further, the length "L3" of the stylet 400 permits the distal portion 410b of the elongated body 410 of the stylet 400 to extend distally beyond a distal end 530a of the threaded shank 530 of the pedicle screw 500 when the extension assembly 300 and the pedicle screw 500 are operatively coupled to the driving assembly 200 and the handle assembly 100, as shown in FIGS. 1, 3, and 4. In a non-limiting embodiment, it is contemplated that the distal portion 410b of the elongated body 410 of the stylet 400 protrudes approximately 10 millimeters beyond the distal end 530a of the threaded shank 530 of the pedicle screw 500. In alternative embodiments, it is contemplated that the distal portion 410b of the elongated body 410 of the stylet 400 may be extendable any length suitable for its intended purpose.

Specifically, the tissue engaging member 414 at the distal portion 410b of the elongated body 410 of the stylet 400 is configured to facilitate introduction of the pedicle screw 500 into vertebral bone "VB" without the need for additional instruments, such as, for example, a guidewire or the like. In embodiments, the tissue engaging member 414 of the stylet 400 may include a beveled, tapered, or diamond shaped end to facilitate penetration of the vertebral bone "VB." Alternatively, the tissue engaging member 414 of the stylet 400 may include any suitable configuration configured to facilitate penetration of the vertebral bone "VB." Additionally, it is contemplated that the elongated body 410 of the stylet 400 may include any suitable wire diameter configured to penetrate vertebral bone "VB" and begin a pilot hole/pathway to facilitate introduction of the pedicle screw 500 into the vertebral bone "VB."

Figure 2:
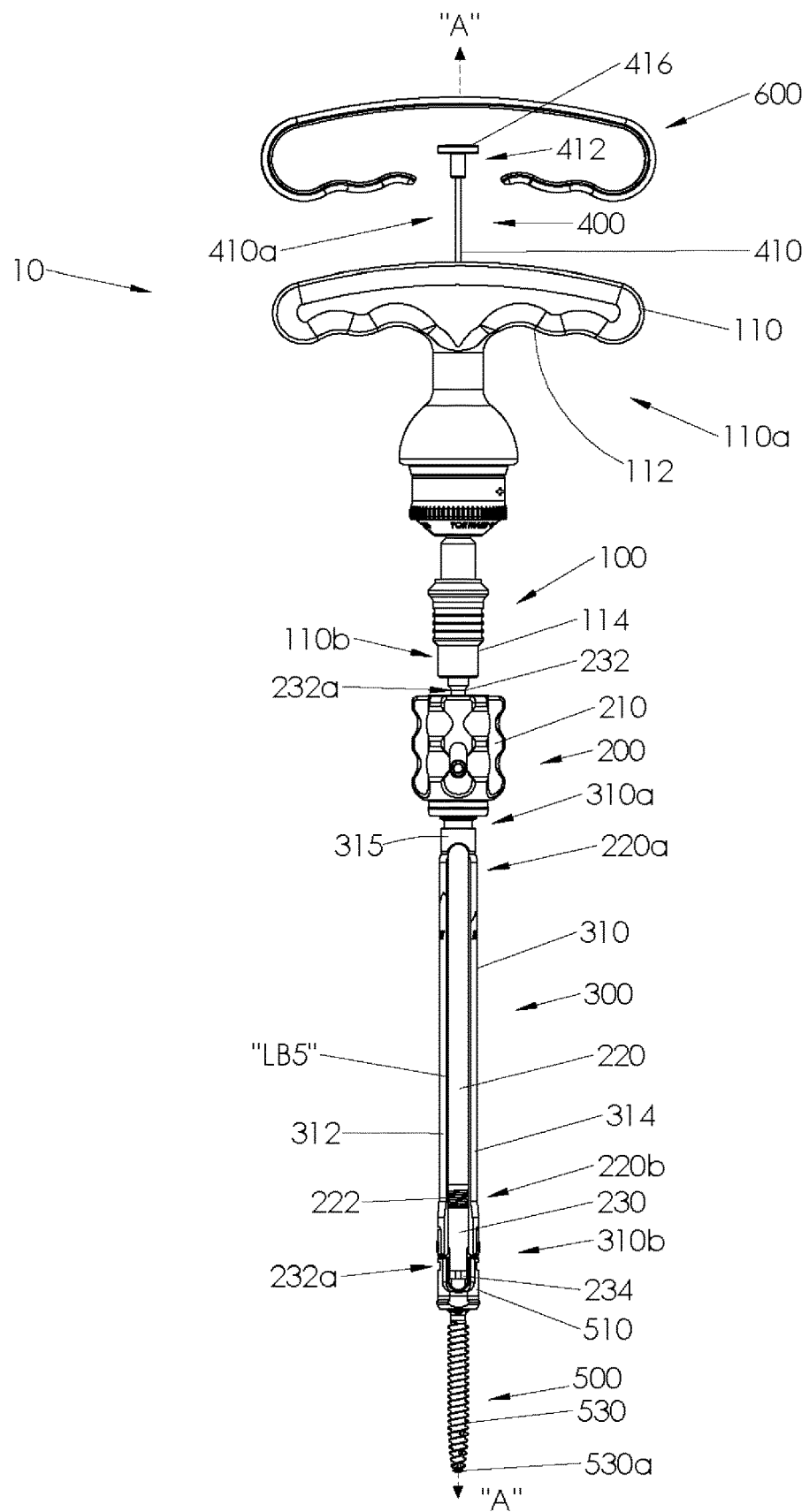
FIG. 2 is a front view of the screw insertion instrument and the pedicle screw of FIG. 1, showing a clamping member separated and a stylet partially retracted.

As illustrated in FIGS. 2 and 4, in embodiments, the head 412 of the stylet 400 includes a cap or flange 416 having a diameter that is greater than the diameter of the first longitudinal bore "LB1" of the ratcheting handle 110 such that when the stylet 400 is advanced distally through the first longitudinal bore "LB1" of the ratcheting handle 110 of the handle assembly 100 and the second longitudinal bore "LB2" of the elongated body 232 of the driver 230, the flange 416 of the stylet 400 prevents further distal translation of the stylet 400 once the flange 416 of the stylet 400 abuts the proximal portion 110a of the ratcheting handle 110 of the handle assembly 100.

Figure 5:
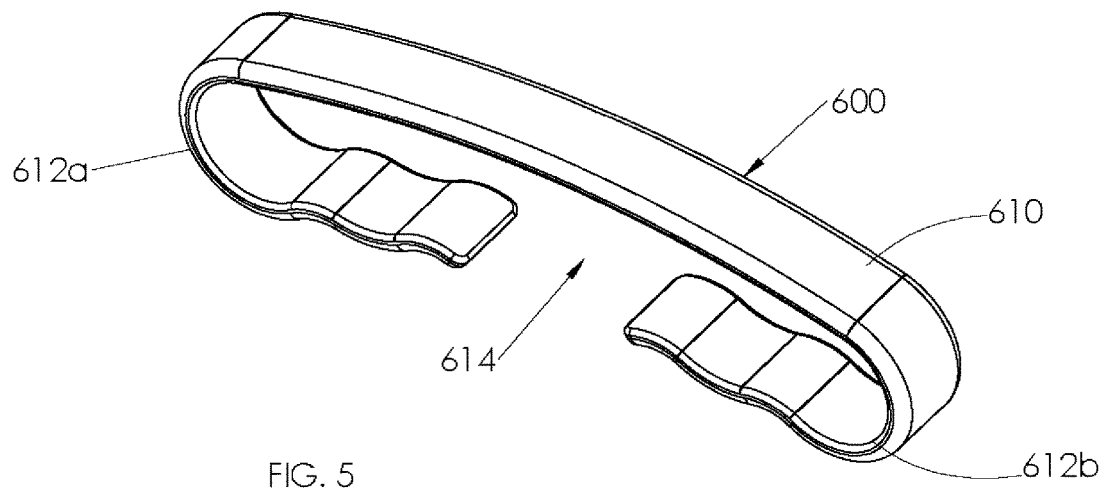
FIG. 5 is a perspective view of a clamping member of the screw insertion instrument of FIG. 1.
Figure 6:
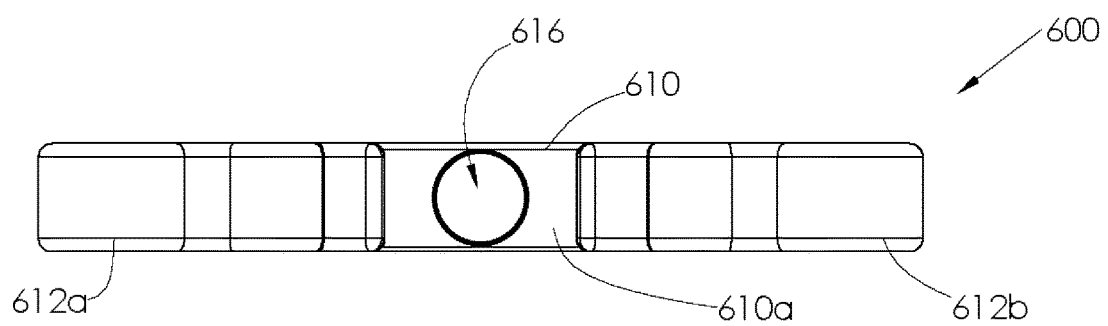
FIG. 6 is a bottom view of the clamping member of FIG. 5.

With continued reference to FIGS. 1-4, and additional reference to FIGS. 5 and 6, in embodiments, the screw insertion instrument 10 includes a clamping member 600 configured to be selectively disposed over the proximal portion 110a of the ratcheting handle 110 of the handle assembly 100 to translatably secure the stylet 400 within the first longitudinal bore "LB1" of the ratcheting handle 110 of the handle assembly 100.

As illustrated in FIG. 5, in embodiments, the clamping member 600 is substantially C-shaped and includes a body 610 having a pair of wings 612a, 612b extending from opposing portions of the body 610 and towards one another to define a handle-receiving passage 614. In embodiments, the clamping member 600 is contoured to correspond to the configuration of the ratcheting handle 110. Specifically, the pair of wings 612a, 612b includes a configuration corresponding to the shape of the gripping portion 112 of the ratcheting handle 110 such that when the clamping member 600 is disposed over the ratcheting handle 110, the clamped ratcheting handle 110 (see e.g., FIG. 1) provides ample finger grip leverage to help the clinician grip the ratcheting handle 110 during operation. Further, it is contemplated that the pair of wings 612a, 612b are resiliently biased towards a bottom or handle-facing surface 610a of the body 610 of the clamping member 600 (see FIG. 6) such that upon positioning the clamping member 600 over the ratcheting handle 110 of the handle assembly 100, wherein the ratcheting handle 110 is disposed within the handle-receiving passage 614 of the clamping member 600, the ratcheting handle 110 is clamped between the pair of wings 612a, 612b and the body 610 of clamping member 600.

As illustrated in FIG. 6, in embodiments, the handle-facing surface 610a of the body 610 of the clamping member 600 includes a recess 616 sized and shaped to receive the flange 416 of the stylet 400 (see e.g., FIG. 4) when the stylet 400 is disposed within the first longitudinal bore "LB1" of the ratcheting handle 110 of the handle assembly 100 and the clamping member 600 is positioned over the ratcheting handle 110. It is contemplated that a depth of the recess 616 may be approximately equal to a height of the flange 416. As such, with the flange 416 of the stylet 400 located within the recess 616 of the clamping member 600 (FIG. 4), the handle-facing surface 610a of the clamping member 600 is permitted to frictionally engage the proximal portion 110a of the ratcheting handle 110 to help secure the ratcheting handle 110 within the handle-receiving passage 614 of the clamping member 600.

With reference to FIGS. 1-4, in operation, a clinician employs the screw insertion instrument 10 to mount and/or secure the pedicle screw 500 in the vertebral bone "VB." First, the clinician grasps the elongated body 310 of the extension assembly 300, with the pedicle screw 500 coupled thereto, and advances the handle assembly 100, with the driving assembly 200 coupled thereto, distally such that the tubular body 220 of the driving assembly 200 is advanced through the fifth longitudinal bore "LB5" of the elongated body 310 of the extension assembly 300 until the driving bit 234 of driver 230 of the driving assembly 200 engages the head 510 of the pedicle screw 500. Next, the clinician rotates the knob 210 of the driving assembly 200 in the clockwise direction "B1" (FIG. 3) relative to the longitudinal axis "A-A" to threadably engage the distal section 210b of the knob 210 with the proximal portion 310a of the elongated body 310. The knob 210 is then moved to the proximal position relative to the tubular body 220 to securely fix the handle assembly 100, the driving assembly 200, the extension assembly 300, and the pedicle screw 500.

Next, the clinician advances the stylet 400 distally through the first longitudinal bore "LB1" of the ratcheting handle 110 of the handle assembly 100 and the second longitudinal bore "LB2" of the elongated body 232 of the driver 230 until the flange 416 of the stylet 400 abuts the proximal portion 110a of the ratcheting handle 110 of the handle assembly 100 and the distal portion 410b of the elongated body 410 of the stylet 400 extends distally beyond a distal end 530a of the threaded shank 530 of the pedicle screw 500. Then, the clamping member 600 is disposed over the proximal portion 110a of the ratcheting handle 110 of the handle assembly 100 to secure the stylet 400 within the first longitudinal bore "LB1" of the ratcheting handle 110 of the handle assembly 100.

As such, the screw insertion instrument 10 and the pedicle screw 500 are locked together with the stylet 400 extending therethrough, affording the clinician better control over the placement of the pedicle screw 500 within the vertebral bone "VB," without the need for additional instruments, such as, for example, a guidewire or the like. Once the pedicle screw 500 is properly located by the clinician, the clinician may penetrate the vertebral bone "VB" with the tissue engaging member 414 at the distal portion 410b of the elongated body 410 of the stylet 400 to facilitate introduction of the pedicle screw 500 into the vertebral bone "VB."

This process may be repeated as many times as the clinician desires, whether it be for the same pedicle screw 500 or for a plurality of pedicle screws 500 as part of the procedure being performed. To unlock the handle assembly 100 and the driving assembly 200 from the extension assembly 300 and the pedicle screw 500, the clinician grasps the elongated body 310 of the extension assembly 300 and rotates the knob 210 of the driving assembly 200 in a counter-clockwise direction "B2" (FIG. 3) relative to the longitudinal axis "A-A" to threadably disengage the distal section 210b of the knob 210 with the proximal portion 310a of the elongated body 310. The knob 210 may then be moved to the distal position relative to the tubular body 220 to unlock the handle assembly 100 and the driving assembly 200 from the extension assembly 300 and the pedicle screw 500.

Referring now to FIGS. 7-12, a screw insertion instrument in accordance with another embodiment of the present disclosure is shown and generally designated as 10'. Similar to the screw insertion instrument 10, the screw insertion instrument 10' generally includes a handle assembly 100', a driving assembly 200, an extension assembly 300, a stylet 400', and optionally, a spacer 700, selectively coupled to a pedicle screw 500, and which are all coaxially aligned along a longitudinal axis "A1-A1". Accordingly, the screw insertion instrument 10' is only described herein to the extent necessary to describe the differences in construction and operation thereof.

The handle assembly 100' includes a ratcheting handle 110' similar to the ratcheting handle 110 of the handle assembly 100. The ratcheting handle 110' of the handle assembly 100' defines a first longitudinal bore "LB1'" (FIG. 9) similar to the first longitudinal bore "LB1" of the ratcheting handle 110 of the handle assembly 100. The first longitudinal bore "LB1'" of the ratcheting handle 110' includes a threaded inner surface 110c adjacent a proximal portion 110a of the ratcheting handle 110', as will be further detailed below.

Figure 10:
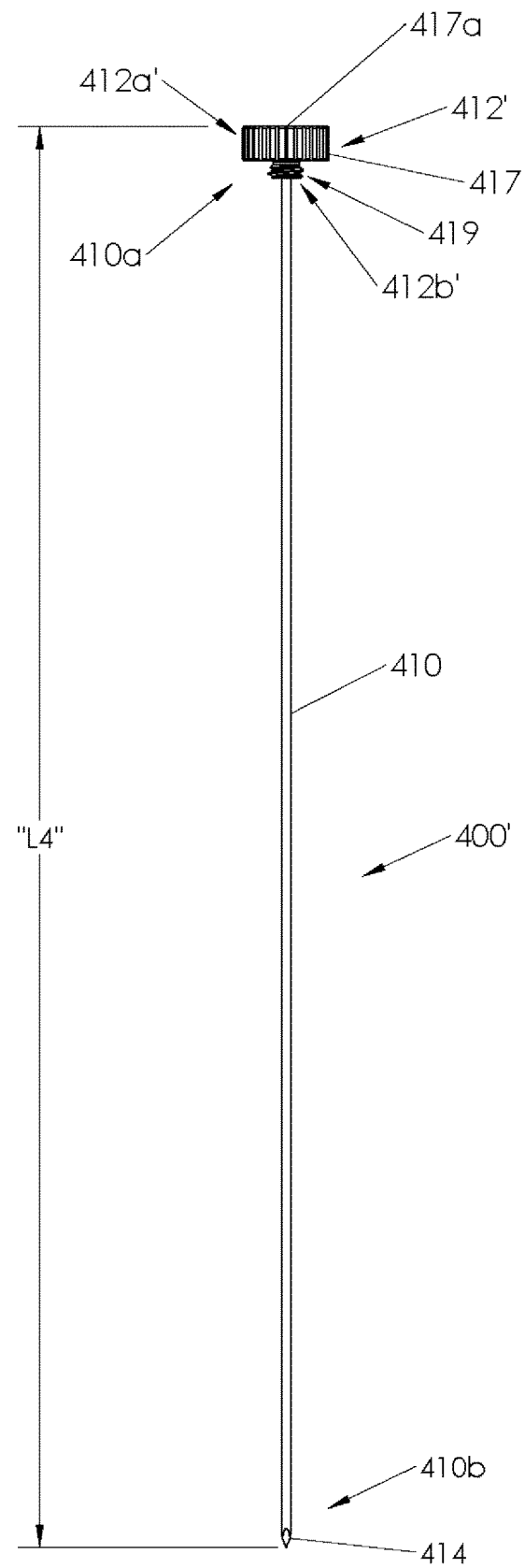
FIG. 10 is a side view of a stylet of the screw insertion instrument of FIG. 8.

As specifically shown in FIG. 10, the stylet 400' includes an elongated body 410 having a proximal portion 410a and a distal portion 410b. In embodiments, the proximal portion 410a of the elongated body 410 includes a head 412' and the distal portion 410b of the elongated body 410 includes a tissue engaging member 414. In embodiments, the head 412' of the elongated body 410 of the stylet 400' includes a knob 417 at a proximal region 412a' thereof and a threaded portion 419 at a distal region 412b' thereof. The knob 417 includes a crenellated outer surface 417a configured to enable a clinician to easily handle and grip the knob 417.

Figure 7:
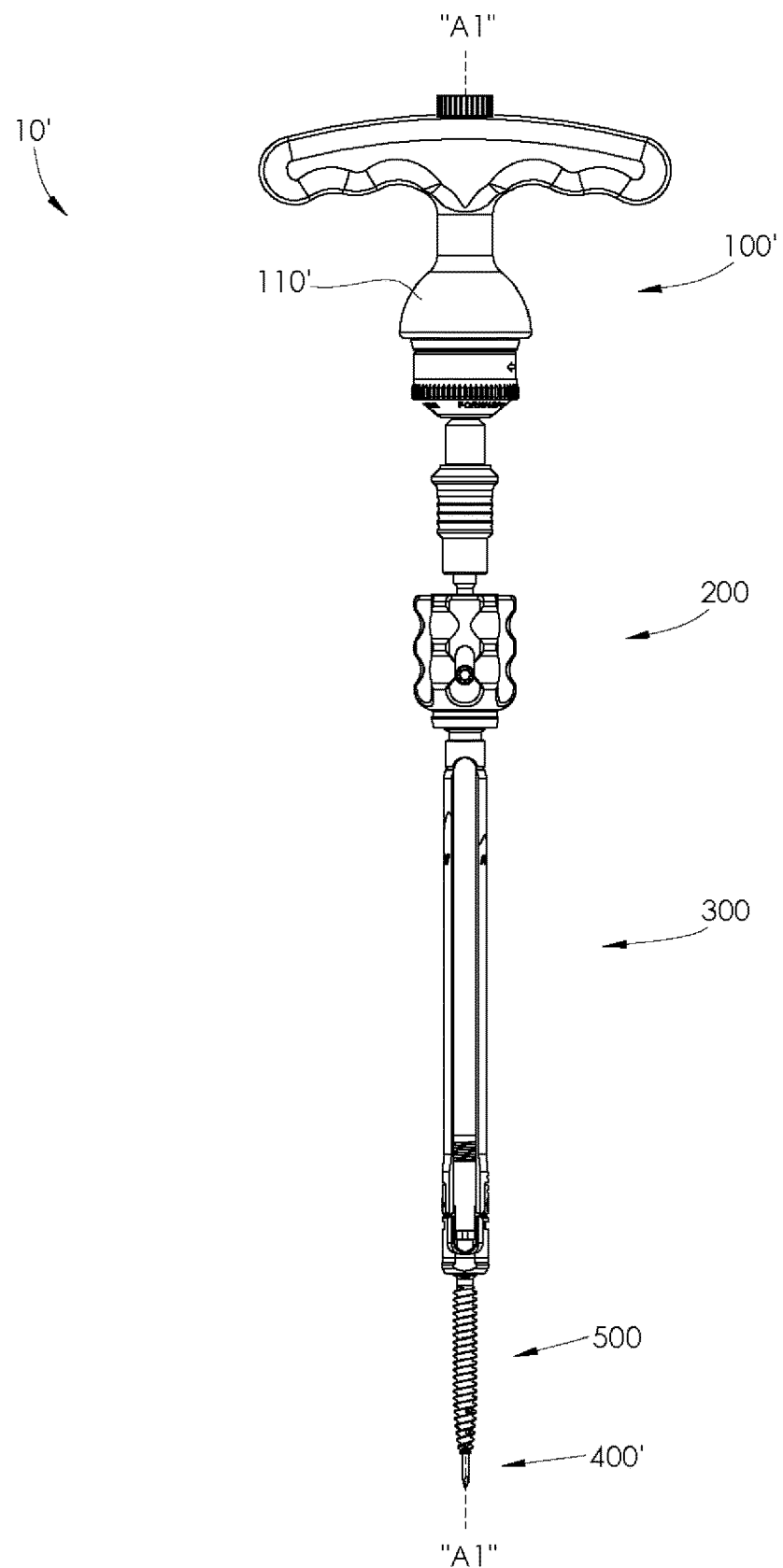
FIG. 7 is a front view of a screw insertion instrument and a pedicle screw in accordance with another embodiment of the present disclosure.

In an embodiment of use, when the stylet 400' is disposed within the first longitudinal bore "LB1'" of the ratcheting handle 110', the threaded portion 419 of the stylet 400' is configured to threadably engage the threaded inner surface 110c adjacent the proximal portion 110a of the ratcheting handle 110' to selectively secure the stylet 400' within the handle assembly 100', as shown in FIG. 7. In an embodiment of use in which the screw insertion instrument 10' is utilized with the spacer 700, as shown in FIGS. 8 and 9, when the stylet 400' is disposed within the first longitudinal bore "LB1'" of the ratcheting handle 110', the stylet 400' is configured to threadably engage the spacer 700 which, in turn, is configured to threadably engage the ratcheting handle 110', as will be further detailed below.

As shown in FIGS. 8 and 9, the spacer 700 is configured to be disposed between the proximal portion 110a of the ratcheting handle 110' and the head 412' of the stylet 400' such that a predetermined length of the distal portion 410b of the elongated body 410 of the stylet 400' extends distally beyond the distal end 530a of the threaded shank 530 of the pedicle screw 500. It is contemplated that the spacer 700 may facilitate the use of the stylet 400' having a length "L4" (FIG. 10) with pedicle screws 500 having various lengths, while maintaining the predetermined length of the distal portion 410b of the elongated body 410 of the stylet 400' that extends distally beyond the distal end 530a of the threaded shank 530 of the pedicle screw 500.

For example, in a non-limiting embodiment, if the length "L4" of the stylet 400' is sized to be used for a 55 millimeter pedicle screw 500 such that a predetermined length of approximately 10 millimeters of the distal portion 410b of the stylet 400' protrudes distally beyond the distal end 530a of the threaded shank 530 of the pedicle screw 500, a 35 millimeter pedicle screw 500 may be used with a 55/35 spacer 700 such that the predetermined length of approximately 10 millimeters is maintained. Additionally and/or alternatively, the spacer 700 may be rotated about the longitudinal axis "A1-A1" relative to the ratcheting handle 110' to adjust the length of the distal portion 410b of elongated body 410 of the stylet 400' that extends distally beyond the distal end 530a of the threaded shank 530 of the pedicle screw 500.

Figure 11:
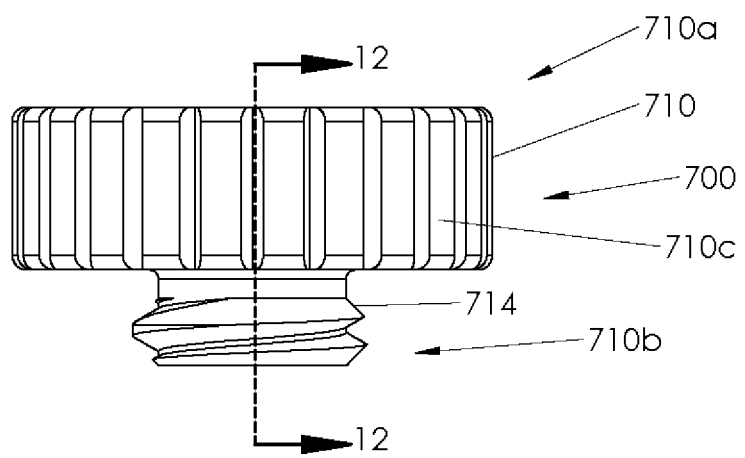
FIG. 11 is a front view of the spacer of the screw insertion instrument of FIG. 8.
Figure 12:
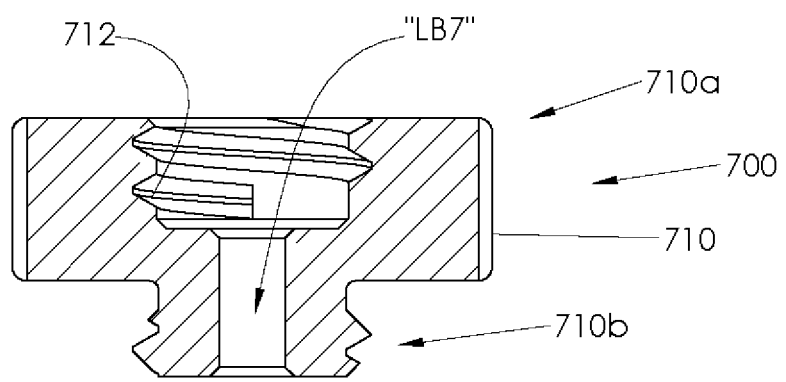
FIG. 12 is a cross-sectional view of the spacer of FIG. 11, taken along section line 12-12 of FIG. 11.

As specifically shown in FIGS. 11 and 12, the spacer 700 includes a body 710 having a proximal section 710a and a distal section 710b. In embodiments, the body 710 of the spacer 700 includes a crenellated outer surface 710c configured to enable a clinician to easily handle and grip the spacer 700.

The body 710 of the spacer 700 defines a seventh longitudinal bore "LB7" extending between the proximal section 710a and the distal section 710b thereof. The seventh longitudinal bore "LB7" of the spacer 700 is coaxially aligned along the longitudinal axis "A1-A1" and includes a diameter configured to rotatably and translatably support the stylet 400'. In embodiments, the proximal section 710a of the spacer 700 includes an inner threaded surface 712 configured to threadably engage the threaded portion 419 of stylet 400' (FIG. 9) to operatively secure the stylet 400' to the ratcheting handle 110' via the spacer 700. In embodiments, the distal section 710b of the spacer 700 includes a threaded outer surface 714 configured to threadably engage the threaded inner surface 110c adjacent the proximal portion 110a of the ratcheting handle 110' (FIG. 9).

It will be understood that various modifications may be made to the embodiments of the presently disclosed screw insertion instrument. For example, in embodiments, the stylet 400, 400' and the spacer 700 of the presently disclosed screw insertion instrument may be used in conjunction with a bone tap instrument to facilitate introduction of the bone tap instrument into vertebral bone "VB" where the bone tap is used in lieu of a bone screw. Therefore, the above description should not be construed as limiting, but merely as exemplifications of embodiments. Those skilled in the art will envision other modifications within the scope and spirit of the present disclosure.

What is claimed is:

1. A method for inserting a screw into vertebral bone, the method comprising:
   advancing a driving assembly through an extension assembly that is coupled to a pedicle screw such that a knob of the driving assembly abuts a proximal portion of the extension assembly, a tubular body of the driving assembly is disposed within the extension assembly, and a driving bit of a driver of the driving assembly engages a head of the pedicle screw;

advancing a stylet distally through a handle that is coupled to the driver of the driving assembly such that when an elongated body of the stylet is positioned through the handle, the driver, and the pedicle screw, a flange of the stylet abuts a proximal facing surface of the handle, and a distal portion of the stylet extends distally beyond a distal end of the pedicle screw;

translating a retainer relative to the handle such that a first portion of the retainer passes distally of a surface of the handle and a second portion of the retainer passes proximally of a surface of the flange and the retainer thereby retains the flange in abutment with the handle;

penetrating vertebral bone with the distal portion of the stylet to create a pilot hole; and introducing the pedicle screw into the vertebral bone through the pilot hole.

2. The method according to claim 1, further including:

rotating the knob of the driving assembly to secure the extension assembly to the driving assembly; and actuating the knob of the driving assembly to rotatably fix the driver to the knob; wherein the driver includes a splined surface and the knob includes a laterally biased spline element, and actuating the knob includes moving the knob relative to the driver such that the spline element is biased into splined engagement with the splined surface.

3. The method of claim 1, further comprising threadingly engaging two extensions of the extension assembly with a threaded portion of the tubular body.

4. The method of claim 2, including rotating the knob relative to the extension assembly to threadably disengage the knob from the extension assembly after introducing the pedicle screw into the vertebral bone.

5. The method of claim 1, wherein the step of penetrating the vertebral bone includes transmission of force to the stylet through abutment between the retainer and the flange.

6. The method of claim 1, wherein the retainer, when positioned to retain the flange in abutment with the handle, prevents proximal movement of the flange relative to the handle absent deformation of the retainer.

7. The method of claim 1, wherein during the step of penetrating the vertebral bone the retainer resists proximal movement of the stylet.

8. A method for inserting a screw into an object, the method comprising:

advancing a stylet distally through a handle that is coupled to a driver of a driving assembly such that when an elongated body of the stylet is positioned through the handle, the driver, and a screw engaged by the driver, a flange of the stylet abuts a proximal facing surface of the handle, and a distal portion of the stylet extends distally beyond a distal end of the screw;

translating a retainer relative to the handle such that a first portion of the retainer passes distally of a surface of the handle and a second portion of the retainer passes proximally of a surface of the flange and the retainer thereby restricts proximal movement of the stylet relative to the handle;

penetrating the object with the distal portion of the stylet to create a pilot hole while the retainer abuts the flange; and introducing the screw into the object through the pilot hole.

9. The method of claim 8, further comprising coupling an extension assembly that is coupled to the screw to the driving assembly.

10. The method of claim 9, wherein the coupling an extension assembly to the driving assembly includes rotating a knob of the driving assembly to threadably engage the knob to the extension assembly.

11. The method of claim 10, comprising threadably disengaging the knob from the extension assembly after introducing the screw into the object.

12. The method of claim 11, including engaging a distal end of the driver to a second screw after threadably disengaging the knob from the extension assembly.

13. The method of claim 9, including advancing the driving assembly distally through the extension assembly before coupling the driving assembly to the extension assembly.

14. The method of claim 8, wherein the handle includes a recess, and the flange of the stylus abuts the proximal facing surface of the handle within the recess.

15. The method of claim 8, the step of translating the retainer places the retainer such that the flange simultaneously abuts the handle and the retainer.

* * * * *